US011819397B2

(12) United States Patent
Roell et al.

(10) Patent No.: US 11,819,397 B2
(45) Date of Patent: Nov. 21, 2023

(54) ABSORBENT ARTICLE WITH ADHESIVE PATTERN

(71) Applicant: The Procter & Gamble Company, Cincinnati, OH (US)

(72) Inventors: Stefan Roell, Bensheim (DE); John Ferrer, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 906 days.

(21) Appl. No.: 16/809,601

(22) Filed: Mar. 5, 2020

(65) Prior Publication Data

US 2020/0281782 A1 Sep. 10, 2020

Related U.S. Application Data

(60) Provisional application No. 62/813,824, filed on Mar. 5, 2019.

(51) Int. Cl.
*A61F 13/56* (2006.01)
*A61F 13/472* (2006.01)
*A61F 13/514* (2006.01)

(52) U.S. Cl.
CPC ........ *A61F 13/5611* (2013.01); *A61F 13/472* (2013.01); *A61F 13/51456* (2013.01); *A61F 2013/5147* (2013.01)

(58) Field of Classification Search
CPC .............. A61F 13/472; A61F 13/51456; A61F 13/5611; A61F 2013/5147
See application file for complete search history.

(56) References Cited

U.S. PATENT DOCUMENTS

| 4,336,804 | A | * | 6/1982 | Roeder | ............... A61F 13/5611 604/387 |
| 4,690,680 | A | | 9/1987 | Higgins | |
| 5,578,026 | A | | 11/1996 | Lavash | |
| 5,591,153 | A | | 1/1997 | Mattingly, III | |
| D460,177 | S | * | 7/2002 | Endo | ............................. D24/125 |
| D460,819 | S | * | 7/2002 | Endo | ............................. D24/124 |

(Continued)

FOREIGN PATENT DOCUMENTS

| CN | 1207666 A | 2/1999 |
| CN | 1625377 A | 6/2005 |

(Continued)

OTHER PUBLICATIONS

PCT Search Report and Written Opinion for PCT/US2020/021066 dated Jun. 24, 2020.

*Primary Examiner* — Susan S Su
(74) *Attorney, Agent, or Firm* — Amanda Herman Berghauer; George Henry Leal

(57) ABSTRACT

An absorbent article having a front section, a central section and a rear section located along a longitudinal axis is described. A first pattern of adhesive is applied to the central section of a garment facing surface of the backsheet. The first pattern of adhesive has a first plurality of stripes extending substantially parallel to the transverse axis on a first side of the central longitudinal axis. A second plurality of stripes extends substantially parallel to the transverse axis on a second side of the central longitudinal axis. A first gap between the first plurality of stripes and the second plurality of stripes extends over the central longitudinal axis.

10 Claims, 10 Drawing Sheets

(56) References Cited

U.S. PATENT DOCUMENTS

| | | | |
|---|---|---|---|
| 6,443,836 B1 | | 9/2002 | Horejsi |
| D465,278 S | * | 11/2002 | Endo .......................... D24/125 |
| 9,439,817 B2 | * | 9/2016 | Nishimura .......... A61F 13/5611 |
| 11,058,590 B2 | * | 7/2021 | Toro ...................... A61F 13/514 |
| 2009/0062761 A1 | * | 3/2009 | Goerg-Wood ...... A61F 13/5611 |
| | | | 604/385.01 |
| 2010/0191210 A1 | | 7/2010 | Hayashi |
| 2011/0028927 A1 | | 2/2011 | Bellucci et al. |

FOREIGN PATENT DOCUMENTS

| | | |
|---|---|---|
| DE | 19957053 A1 | 5/2007 |
| EP | 0471384 A1 | 2/1992 |
| EP | 1190691 B1 | 7/2009 |
| JP | 2003010245 A | 1/2003 |
| JP | 2006247088 A | 9/2006 |
| JP | 2006296974 A | 11/2006 |
| JP | 2007130274 A | 5/2007 |
| JP | 2007135660 A | 6/2007 |
| JP | 2007135661 A | 6/2007 |
| JP | 2007236552 A | 9/2007 |
| JP | 2009207716 A | 9/2009 |
| JP | 2012050716 A | 3/2012 |
| JP | 2015160066 A | 9/2015 |
| WO | WO9204000 A1 | 3/1992 |
| WO | WO0139708 A2 | 6/2001 |
| WO | WO2016100041 A1 | 6/2016 |

* cited by examiner

ABSORBENT ARTICLE WITH ADHESIVE PATTERN

FIELD OF THE INVENTION

The present invention relates to absorbent articles comprising a patterned application of fastening adhesive on the garment facing side of the backsheet, the new pattern providing enhanced fit and comfort while reducing the amount of adhesive used.

BACKGROUND OF THE INVENTION

Absorbent articles for personal hygiene which during use are attached to the underwear of the user are known in the art. Typical examples include sanitary napkins, pantyliners and incontinence pads. Such articles are commonly used to absorb and retain bodily fluids and other exudates excreted by the human body, such as urine and menses. These absorbent articles typically comprise a topsheet, a backsheet, and, optionally, an absorbent core disposed between the topsheet and backsheet and a fastening adhesive applied on the garment facing surface of the backsheet and are disposable after single use.

The fastening adhesive can have a surprisingly instrumental impact on absorbent articles, from multiple perspectives, for example: the adhesion of a sanitary napkin to a user's undergarments (from the perspective of retention of the pad in position during use and for the ease of removal of the pad) and the comfort experienced by a user while the pad is in situ. In this respect, sufficient adhesive is required to properly secure the pad in position, particularly while a user is moving. However, the amount of adhesive used has an impact on the overall stiffness of the pad and this, in turn, can render a sanitary napkin uncomfortable to use.

Further issues related to the amount and placement of adhesive on the underside of a sanitary napkin include the force required to peel the sanitary napkin off from an undergarment to which it is attached. If the force required is too high, there is a risk of the backsheet of the sanitary napkin tearing. This is highly undesirable because a torn backsheet exposes the content of the absorbent core thus creating a hygienic problem, and additionally fragments of backsheet may firmly stick to the undergarment and may be very difficult to remove in the absence of a graspable portion which can be used to peel off the fragment.

Furthermore, oftentimes, a silicone coated film or wrapper is attached to the adhesive on the underside of a sanitary napkin prior to use. It is desirable if the force required to remove this film or wrapper is not excessive, while again, ensuring sufficient adhesive for properly adhering the sanitary napkin to a user's undergarments. Thus, there are many factors that must be considered when designing an appropriate pattern of fastening adhesive.

WO 2016/100041 describes a discontinuous pattern of fastening adhesive applied to the garment facing surface of an absorbent article. This pattern enables use of a thinner than usual backsheet by reducing the force needed to remove the absorbent article from a user's undergarments. The reduced and distributed force reduces the likelihood that the backsheet would tear during removal. While this pattern goes some way towards improving the removal of an absorbent article from a user's undergarments without compromising on the adhesive properties, it does not provide any additional benefits in terms of comfort.

There is therefore a need to identify an improved backsheet/fastening adhesive combination which is strong enough to keep the article in place during its usage and which at the same time provides for greater comfort during use and does not cause rupture of the article when it is removed from an undergarment.

SUMMARY OF THE INVENTION

The present invention relates to an absorbent article having a central longitudinal axis and a transverse axis perpendicular to the longitudinal axis, the absorbent article comprising:
  a) a front section, a central section and a rear section located along the longitudinal axis;
  b) a backsheet having a garment facing surface;
  c) a first pattern of fastening adhesive applied to the central section of the garment facing surface of the backsheet, the first pattern of adhesive comprising:
    i) a first plurality of stripes extending substantially parallel to the transverse axis on a first side of the central longitudinal axis;
    ii) a second plurality of stripes extending substantially parallel to the transverse axis on a second side of the central longitudinal axis; and
    iii) a first gap between the first plurality of stripes and the second plurality of stripes, wherein the first gap extends over the central longitudinal axis.

Absorbent articles such as those described herein have adhesive patterns that retain the absorbent article in place when adhered to a user's undergarments, while improving the comfort experienced by a user when in situ. The specific patterns described ensure adhesive contact between the absorbent article and a user's undergarment in the places where it is most needed, while minimizing the amount of adhesive used in places where flexibility of the absorbent article is desirable. Thus, the adhesive patterns described herein address the currently unmet need with current absorbent articles where adhesive is applied uniformly with no consideration for comfort. Furthermore, the force required to remove absorbent articles featuring the described adhesive patterns from undergarments is less than the force required to remove absorbent articles with conventional adhesive patterns. This means that the absorbent article is easier to remove for the user and is less prone to tearing, which would otherwise be highly undesirable. Finally, the adhesive pattern described herein uses less adhesive than adhesive patterns of the prior art which provides a cost saving while providing a better user experience overall.

DETAILED DESCRIPTION OF THE INVENTION

Figure 1:
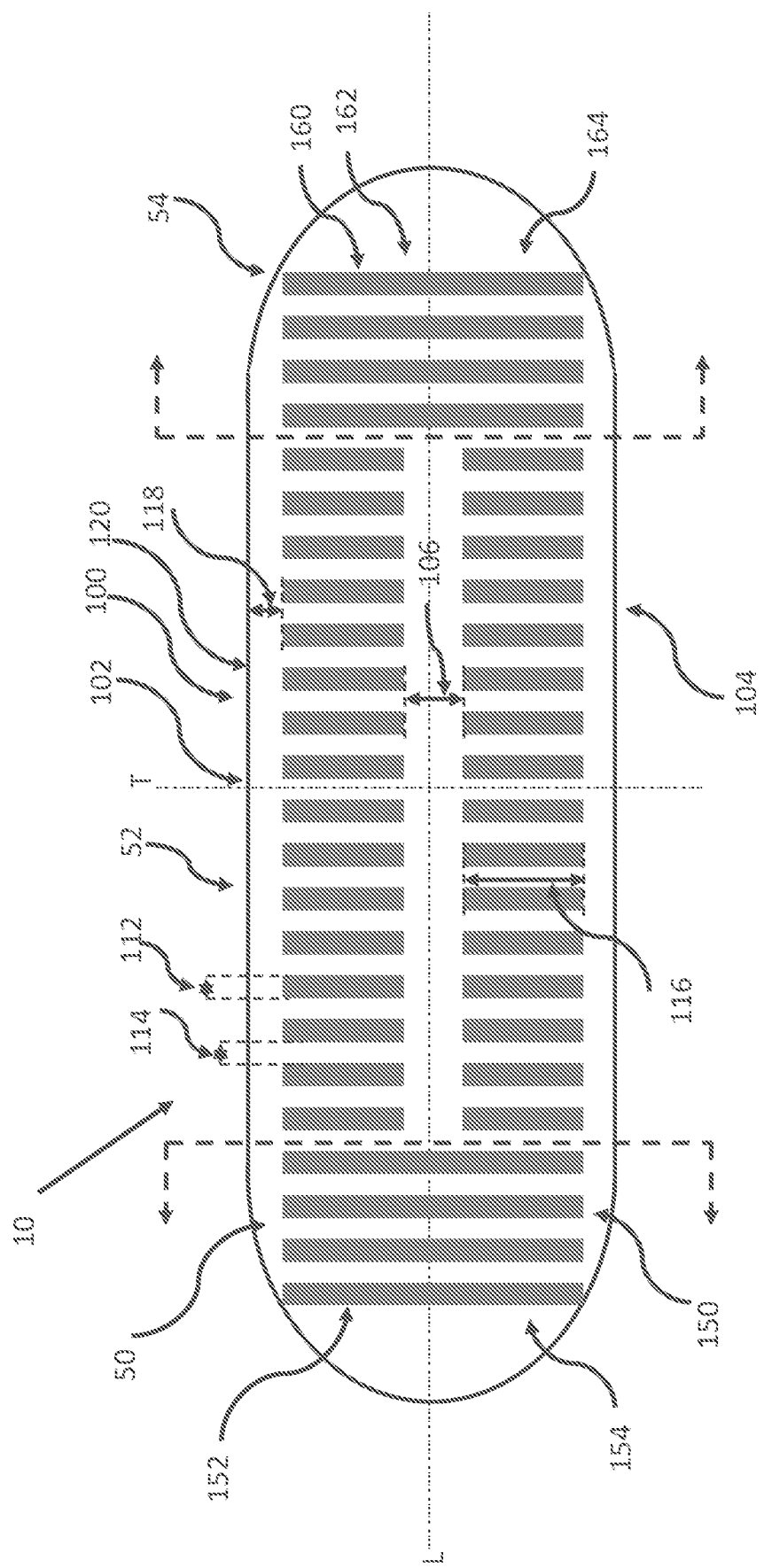
FIG. 1 represents an absorbent article according to the invention.

"Absorbent articles" refers to devices that absorb and contain body exudates, such as urine, menses, and feces. The term "disposable" is used herein to describe absorbent articles which are not intended to be laundered or otherwise restored or reused as an absorbent article after a single use. Examples of absorbent articles include diapers, toddler training pants, adult incontinence garments, and feminine hygiene garments such as sanitary napkins, pantiliners, interlabial devices, hemorrhoid pads, and the like. Absorbent articles according to the present invention are selected from sanitary napkins, incontinence pads and pantyliners.

Absorbent articles and components thereof according to the present invention, including the topsheet, backsheet, absorbent core, and any individual layers of these components, have a body-facing surface and a garment-facing surface. As used herein, "body-facing surface" means that surface of the article or component which is intended to be worn toward or adjacent to the body of the wearer, while the "garment-facing surface" is on the opposite side and is intended to be worn toward or placed adjacent to the wearer's undergarments when the disposable absorbent article is worn.

In general, the absorbent articles of the present invention comprise a topsheet, a backsheet, and (with the exception of thin pantyliners which are not meant to absorb fluids but just to provide a clean feeling to the panties) an absorbent core disposed between the topsheet and backsheet and eventually other optional intermediate layers.

The term "longitudinal", as used herein, refers to a line, axis, or direction in the plane of the absorbent article that is generally aligned with (i.e., approximately parallel to) a vertical plane that bisects a standing wearer into left and right body halves when the absorbent article is worn. The term "transverse", as used herein, refers to a line, axis, or direction that generally lies within the plane of the article that is generally perpendicular to the longitudinal direction.

The topsheet of the absorbent article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet and the topsheet may sandwich one or more intermediate layers. These intermediate layers can comprise additional components of the absorbent articles such as typically, an absorbent core and one or more layers having acquisition and/or distribution properties which are typically disposed between absorbent core and topsheet (in which case are sometimes called "secondary topsheets" or between absorbent core and backsheet.

The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

Polyacrylate based materials, typically partially neutralized polymers, are commonly incorporated in absorbent articles and are known as superabsorbent polymers or superabsorbents, and are crosslinked. The polyacrylate material has neutralized, typically with sodium, carboxylate groups hanging off the main polymer chain. In contact with water, the sodium detaches and goes in solution, leaving only carboxyl ions. Being negatively charged, these ions repel one another so that the polymer unwinds and absorbs more and more water, which is instead attracted by the carboxyl ions, as further carboxyl ions become available. The hydrogen in water is trapped by the polyacrylate due to the atomic bonds associated with the polarity forces between the atoms. The cross-links, which bridge different polymer chains, lead to a three dimensional structure, which upon liquid absorption constitutes the swollen gel.

According to an embodiment of the present invention, the absorbent gelling material which can be comprised in the absorbent core can be selected among the polyacrylate based polymers described in the European Patent Application EP 05023061.4, filed on 21 Oct. 2005 in the name of The Procter and Gamble Company. As explained in the referenced application, polyacrylate based materials being very slightly crosslinked, or substantially not crosslinked at all, incorporated in absorbent articles for the absorption of proteinaceous or serous body fluids such as for example menses, blood, plasma, vaginal secretions, and also mucus or milk, but particularly menses or blood, provide an improved absorption and retention capacity for such body fluids, and an improved absorption rate as well, compared to traditional crosslinked superabsorbents.

The absorbent gelling materials can be typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

Absorbent cores may include a core wrap i.e. a thin layer of fluid pervious material (usually a tissue paper or a think nonwoven layer) which wraps the core in order to preserve its integrity during manufacturing of the article and during its use.

The absorbent article can comprise further components such as side cuffs, typically found in incontinence pads, or side wings or side flaps, typically found in sanitary napkins.

The absorbent articles herein are preferably disposable after a single use and are usually commercialized in packages comprising multiple units which in some cases can be individually wrapped.

The backsheet of the absorbent articles of the present invention is the outer layer of the article on the garment facing side. A fastening adhesive (also called PFA: Panty fastening Adhesive) is applied on the garment facing surface of the backsheet. In case the outer layer of the absorbent article on its garment facing side is a composite material (such as a laminate of a film and a nonwoven material) for the purpose of the present invention the term "backsheet" indicates exclusively the outermost layer of the layers forming said composite material. For example in the case of a NW/PE film laminate with the PE film being the outer layer on which garment facing surface the fastening adhesive is applied, for the purpose of the present invention the term "backsheet" indicates exclusively said outer PE film layer. For the purpose of the present invention side flaps/side wings (which are often formed by extensions of one or both of topsheet and backsheet) are not considered part of the backsheet.

The backsheet of the absorbent articles of the present invention is a plastic film and is preferably flexible and soft. As used herein, the term "flexible and soft" refers to materials which are compliant and will readily conform to the general shape and contours of the human body and will give the users a pleasant tactile feel on the skin. The backsheet prevents the exudates absorbed and contained in the absorbent core from wetting articles which contact the absorbent article such as bedsheets, pants, pajamas and undergarments. The backsheet can also be vapor permeable ("breathable"), while remaining fluid impermeable. In this case typically microporous plastic films are used which are water vapor permeable while remaining essentially impermeable to liquids.

According to the present invention the backsheet is a plastic film having a basis weight of less than 24 gsm or less than 20 gsm or less than 18 gsm or less than 15 gsm or less than 13 gsm. Any type of plastic film can be used as backsheets according to the present invention. Suitable films can be formed by a thermoplastic polymeric material and can be obtained by known film making processes. Plastic films can be selected from single layer or multilayer films which are obtainable for example through a single layer extrusion or a multilayer co-extrusion process. For example US20140248484 discloses a method for producing thin plastic films usable as backsheets in the present invention wherein an initial film web made of a thermoplastic polymer material containing a polyethylene matrix, and 1 to 70 parts by weight of polypropylene per 100 parts by weight of polyethylene matrix, is, after being heated, guided through a cooled roll gap whereby the initial film web is heated only until the polyethylene matrix material melts but below the melting temperature of the polypropylene.

The plastic films usable herein as backsheets can comprise a single polymer or a blend of different polymers. In addition to polymers, the plastic films of the present invention can comprise additives such as for example pigments, dyes, chemical additives such as light protectors, anti oxidants, and inert materials such as titanium oxide, calcium carbonate, or also kaolin, diatomaceous earth, or mixtures thereof. The presence of an inert component, typically calcium carbonate, can increase the physical properties of the polymeric film, particularly heat resistance, which can be beneficial in the context of the present invention, where backsheet films are typically heat sealed along the perimeter to the topsheet of the absorbent article. Also inert materials are sometimes included in plastic films which are mechanically stretched when cold so that the inert particles form a network of channels which allows the passage of water vapor while maintaining a good permeability. Such films are normally identified as "microporous films" are suitable as backsheets in the present invention and they can provide improved breathability in the absorbent articles (as known in the art).

The plastic films usable herein as backsheets of the present invention are preferably thermoplastic polyolefin based film. The plastic film for of the present invention can be for example a polyethylene (PE) based film, a polypropylene based (PP) or a PE/PP blend based film.

When it is mentioned that a film is "based" on a polymer (e.g. PE) or on a mixture of polymers (e.g. PE/PP blend), it is intended that the majority of the mass of the film is constituted by the polymer(s) of which is based on, preferably more than 80% wt. even more preferably more than 90% wt. The remaining mass of the film can be formed by other polymers and customary film additives as known in the art.

PFA: as mentioned above, the backsheet forms the garment-facing surface of the absorbent article on which the fastening adhesive is placed. The fastening adhesive (PFA) can comprise any adhesive or glue used in the art for such purposes. These adhesives typically are pressure sensitive and remain tacky well below their application temperature. For example PFA can be pressure sensitive hot melt adhesives.

Prior to use of the absorbent article, the areas being coated with PFA are typically protected from contamination and from adhering to another surface where this is not desired, by a protective cover means such as a silicone coated release paper, a silicone coated plastic film or any other easily removable cover. The protective cover means can be provided as a single piece or in a multitude of pieces, e.g. to cover individual adhesive areas (e.g. on the backsheet and on the wings). The protective cover means can also perform other functions such as provide individualized packaging for the article or provide a disposal function as known in the art. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The PFA may be applied onto the garment-facing surface of the absorbent article, typically the backsheet and/or the wings, using any one of methods well known in the art for this purpose such as slot coating, spraying and roll printing.

One method of applying the PFA to the garment-facing surface of the absorbent article is the direct coating on the backsheet; another method is printing the PFA onto a release paper, which is then pressed onto the garment-facing surface of the absorbent article. Thereby the PFA is transferred from the release paper to the garment-facing surface of the absorbent article. Such a procedure is described in EP 788,338.

The PFA is applied on the backsheet in order to ensure proper stay in place of the absorbent article during use. During use, the absorbent articles attached to the undergarment using the PFA are subject to various types of stress in different directions, so the strength of adhesion of the PFA must be very high in order to avoid any shift of the article. However, the amount and placement of adhesive applied to the backsheet has an impact on the overall fit and feel of the absorbent article when in use. For example, areas of the absorbent article where PFA is applied to the backsheet tend to be stiffer than areas without PFA. Thus, the adhesion requirements need to be balanced with comfort of the article during use.

Contrary to previous uniform block application of adhesive to a backsheet, in the present invention, it has been surprisingly found that applying adhesive only to specific parts of the backsheet can address the balance between comfort and adhesion. In this respect, the inventors have discovered that the adhesion requirements and purpose differ throughout the absorbent article depending on the interaction with the user's body parts. For example, the present inventors have found that the optimal comfort and fit of an absorbent article is obtained when there is a close fit towards the rear of the absorbent article with more flexibility in the central section. Furthermore, applying the adhesive in a striped pattern to specific parts of the backsheet enables the adhesive to be more evenly distributed within individual stripes and provides better peel-off properties, both in relation to the undergarment to which the absorbent article is attached and to any one time cover or wrapper applied to the article prior to use.

Thus, for purposes of application of PFA, an absorbent article 10 can be considered to have at least three sections located in the longitudinal direction. A front section 50, a central section 52 and a rear section 54. The length of the front section may be at least 10%, 15%, 20% or 25% of the total length of the absorbent article. The length of the rear section may be at least 10%, 15%, 20% or 25% of the total length of the absorbent article. As described herein, the width of the absorbent article is measured at the narrowest part of the absorbent article in the respective front, central or rear sections, discounting any wings that are present.

A first pattern 100 of adhesive is applied to the central section of the garment facing surface of the backsheet. The first pattern preferably has a first 102 and second 104 plurality of stripes, with the stripes extending in a direction substantially parallel to the transverse axis T of the absorbent article. The first plurality is located on one side of the central longitudinal axis L and the second plurality is located on the other side of the central longitudinal axis. A first gap 106 extending over the central longitudinal axis is provided between the first and second plurality of stripes, wherein the first gap has a width measured substantially parallel to the transverse axis of between 10 mm to 40 mm, 10 mm to 35 mm, 10 mm to 30 mm, 15 mm to 40 mm, 15 mm to 35 mm, 15 mm to 30 mm, 20 mm to 30 mm, 20 mm to 35 mm or 20 mm to 40 mm.

Individual stripes in the first pattern may have a width 112, measured in a direction parallel to the longitudinal axis, of between 1 mm to 5 mm, 1 mm to 4 mm, 1 mm to 3 mm, 2 mm to 5 mm, 2 mm to 4 mm, 2 mm to 3 mm, 3 mm to 5 mm or 3 mm to 4 mm and a longitudinal gap 114 of between 1 mm and 10 mm, 1 mm to 8 mm, 1 mm to 6 mm, 2 mm to 10 mm, 2 mm to 8 mm, 2 mm to 6 mm, 4 mm to 10 mm, 4 mm to 8 mm or 4 mm to 6 mm between adjacent stripes. Preferably the stripes have a length 116 measured in a direction parallel to the transverse axis of between 5 mm to 30 mm, 5 mm to 25 mm, 5 mm to 20 mm, 5 mm to 15 mm, 10 mm to 30 mm, 10 mm to 25 mm, 10 mm to 20 mm, 15 mm to 30 mm or 15 mm to 25 mm. Preferably, there is a distance 118 of between 10 mm to 60 mm, 10 mm to 50 mm, 10 mm to 40 mm, 10 mm to 30 mm, 20 mm to 60 mm, 20 mm to 50 mm, 20 mm to 40 mm, 30 mm to 60 mm, 30 mm to 50 mm or 30 mm to 40 mm between the outer edge of the first and second plurality of stripes and the longitudinal edge 120 of the absorbent article. Preferably, the stripes of the first and second plurality combined extend between 10% to 85%, 10% to 75%, 10% to 65%, 10% to 50%, 20% to 85%, 20% to 75%, 20% to 65%, 20% to 50%, 30% to 85%, 30% to 75%, 30% to 65% or 30% to 50% of the width of the absorbent article. Preferably, the area of the central section covered by adhesive is between 10% and 85%, 10% to 75%, 10% to 65%, 10% to 50%, 20% to 85%, 20% to 75%, 20% to 65%, 20% to 50%, 30% to 85%, 30% to 75%, 30% to 65% or 30% to 50% of the total area of the central section.

Figure 2:
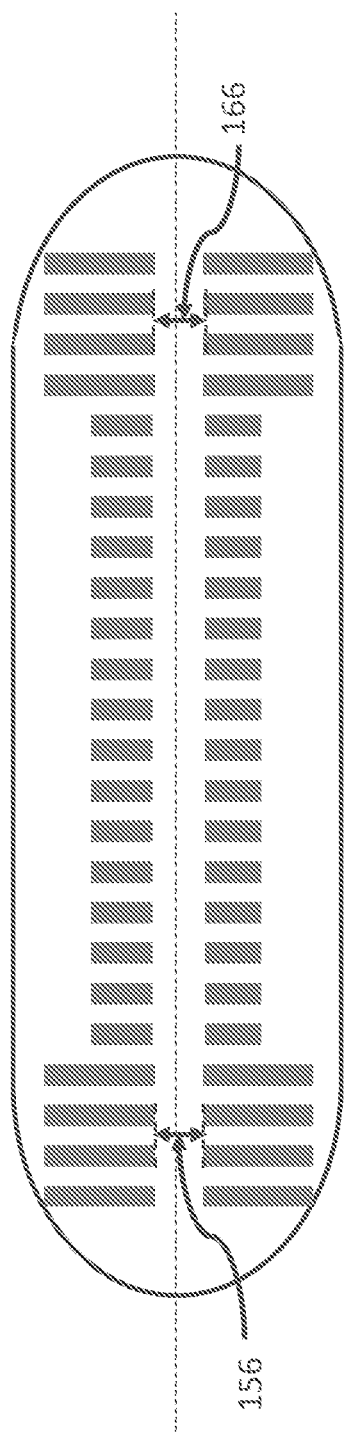
FIGS. 2, 3, 4 and 5 represent absorbent articles of the invention featuring variations to the fastening adhesive pattern.
Figure 3:
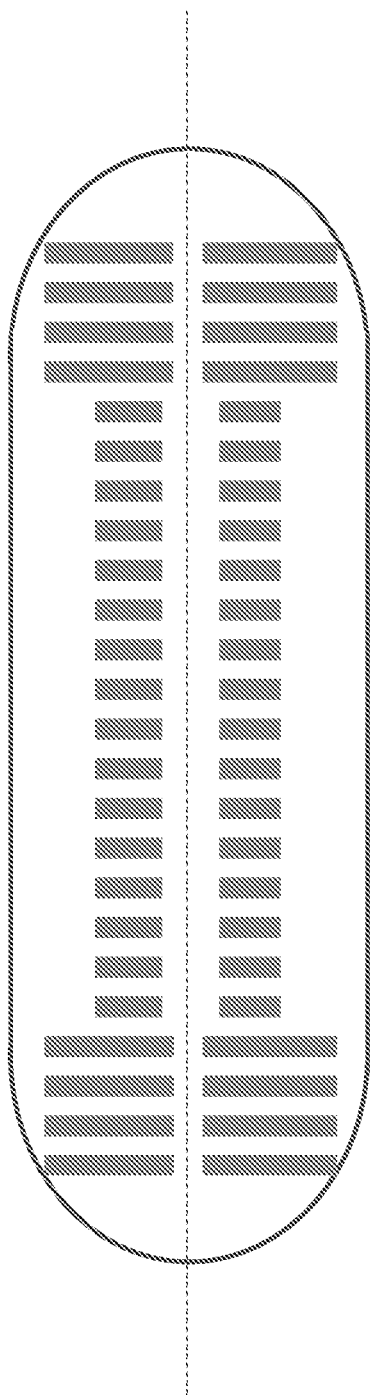

A second pattern 150 of adhesive is applied to the front section of the garment facing surface of the backsheet. The second pattern preferably has a third 152 and fourth 154 plurality of stripes, with the stripes extending in a direction substantially parallel to the transverse axis of the absorbent article. The third plurality is located on one side of the central longitudinal axis and the fourth plurality is located on the other side of the central longitudinal axis with an optional second gap 156 extending over the central longitudinal axis between the third and fourth plurality of stripes, as shown in FIGS. 2 and 3. Alternatively, the third and fourth plurality of stripes may meet at the longitudinal axis such that stripes of the third and fourth pluralities form continuous stripes over the longitudinal axis, as shown in FIGS. 1, 4, 5 and 6.

Figure 4:
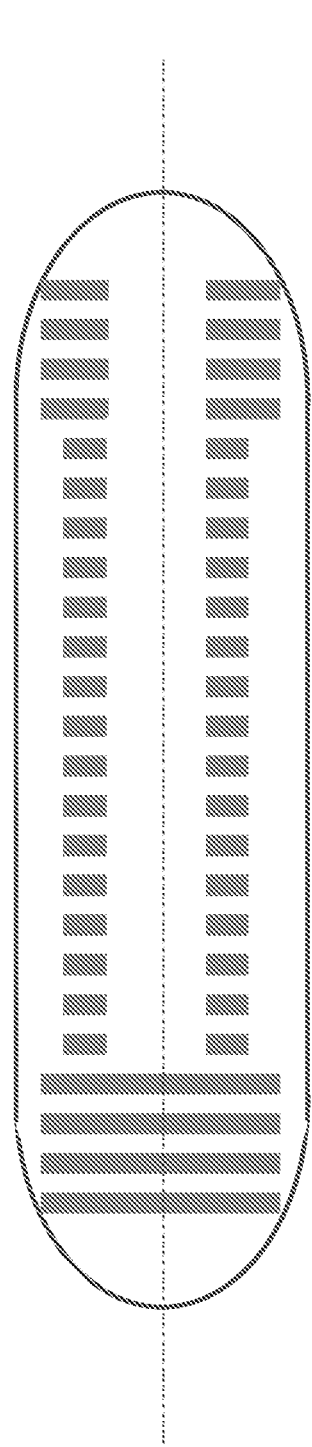
Figure 5:
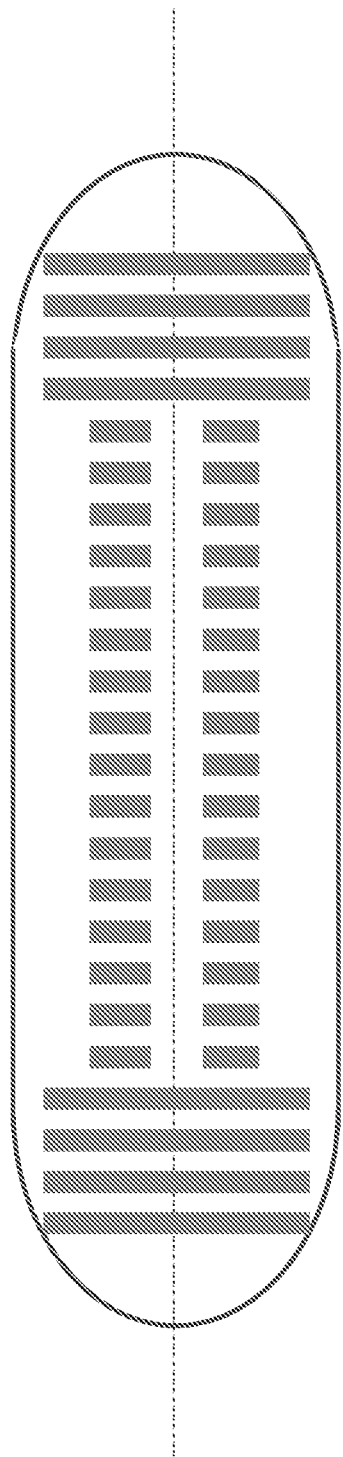

A third pattern 160 of adhesive is applied to the rear section of the garment facing surface of the backsheet. The third pattern preferably has a fifth 162 and sixth 164 plurality of stripes, with the stripes extending in a direction substantially parallel to the transverse axis of the absorbent article. The fifth plurality is located on one side of the central longitudinal axis and the sixth plurality is located on the other side of the central longitudinal axis with an optional third gap 166 extending over the central longitudinal axis between the fifth and sixth plurality of stripes, as shown in FIGS. 2, 3, 4 and 6. Alternatively, the fifth and sixth plurality of stripes may meet at the longitudinal axis such that stripes of the fifth and sixth pluralities form continuous stripes over the longitudinal axis, as shown in FIGS. 1 and 5.

Stripes of the third, fourth, fifth and sixth plurality may have a width, measured in a direction parallel to the longitudinal axis, of between 1 mm to 5 mm and a longitudinal gap of between 1 mm and 10 mm between adjacent stripes. Preferably the stripes have a length measured in a direction parallel to the transverse axis of between 10 mm to 35 mm, 10 mm to 30 mm, 10 mm to 25 mm, 10 mm to 20 mm, 15 mm to 35 mm, 15 mm to 30 mm or 15 mm to 25 mm. Where there is a second and/or third gap, the second or third gap may have a width measured substantially parallel to the transverse axis of between 0.05 mm to 35 mm, 0.5 mm to 35 mm, 5 mm to 35 mm, 10 mm to 35 mm, 10 mm to 30 mm, 10 mm to 25 mm, 10 mm to 20 mm, 15 mm to 35 mm, 15 mm to 30 mm or 15 mm to 25 mm. Alternatively, there may be substantially no second and/or third gap. Preferably, there is a distance of between 10 mm to 60 mm, 10 mm to 50 mm, 10 mm to 40 mm, 10 mm to 30 mm, 20 mm to 60 mm, 20 mm to 50 mm, 20 mm to 40 mm, 30 mm to 60 mm, 30 mm to 50 mm or 30 mm to 40 mm between the outer edge of the respective third, fourth, fifth and sixth pluralities of stripes and the corresponding edge of the absorbent article. Preferably, the stripes of the third and fourth pluralities and the fifth and sixth pluralities combined extend between 20% and 90%, 20% to 75%, 20% to 50%, 35% to 90%, 35% to 75%, 35% to 50%, 50% to 90% or 50% to 75% of the width of the absorbent article. Preferably, the area of the front section covered by adhesive is between 20% and 90%, 20% to 75%, 20% to 50%, 35% to 90%, 35% to 75%, 35% to 50%, 50% to 90% or 50% to 75% of the total area of the front section. Preferably the area of the rear section covered by adhesive is between 20% and 90%, 20% to 75%, 20% to 50%, 35% to 90%, 35% to 75%, 35% to 50%, 50% to 90% or 50% to 75% of the total area of the rear section.

The longitudinal gap between stripes in the third, fourth, fifth and/or sixth pluralities may be between 1 mm and 10 mm, 1 mm to 8 mm, 1 mm to 6 mm, 2 mm to 10 mm, 2 mm to 8 mm, 2 mm to 6 mm, 4 mm to 10 mm, 4 mm to 8 mm or 4 mm to 6 mm. Alternatively, there may be no longitudinal gap between stripes one or more of the third, fourth, fifth and/or sixth pluralities.

The first, second and/or third gaps may have the same or similar widths. Alternatively, the width of the first gap may be less than the width of one or both of the second and third gaps. The distance between the outer edge of the third, fourth, fifth and sixth pluralities may be the same or similar. The distance between the outer edge of the first and second pluralities and the outer edge of the absorbent article may be greater than the distance between the outer edge of the third, fourth, fifth and sixth pluralities and the outer edge of the absorbent article.

The first gap between the first and second pluralities of stripes enables greater flexibility of the central section of the absorbent article when in situ, particularly when the wear is moving. In this respect, the central section of the absorbent article is intended to be located in a user's undergarments in the area nestled between the user's legs. Thus, when the user is upright and moving, the sides of the absorbent article are naturally folded down. Providing a first gap between pluralities of adhesive in the central section allows the absorbent article to more easily fold about the longitudinal axis in this central area where it is required. At the same time, more adhesive may be provided at the front and rear of the absorbent article to ensure the absorbent article remains anchored in place.

FIG. 1 shows an embodiment where the second and third gap are not provided. In such an embodiment, the absorbent article is well anchored at the front and rear while the central section is provided with flexibility. FIGS. 2 and 3 show variations with second and third gaps with differing dimensions. The gaps can be modified to suit the intended use. For example, smaller pads may require a greater proportion of adhesive at the front and/or rear, while for larger pads, the added flexibility provided by the second and third gaps may be preferable. As shown in FIG. 4, in an embodiment one of the second or third gap may be provided while the other is not, or while the other is smaller. In the embodiment shown in FIG. 4, the absorbent article is well anchored at the front, with a very flexible central section and increased adhesive (albeit with a gap) at the rear section. This particular embodiment enables the commonly sought after "W" shape from an absorbent article.

Preferably, the adhesive pattern and/or the mass of adhesive applied to the garment facing surface of the backsheet is symmetrical about the longitudinal axis. Without being bound by theory, it is thought that a symmetrical adhesive pattern provides for uniformity and, accordingly, better securement of the absorbent article to the user's undergarment. The symmetrical nature of the pattern may also provide for easier and more uniform removal of the absorbent article from the wrapper before use or the undergarment after use.

Figure 6:
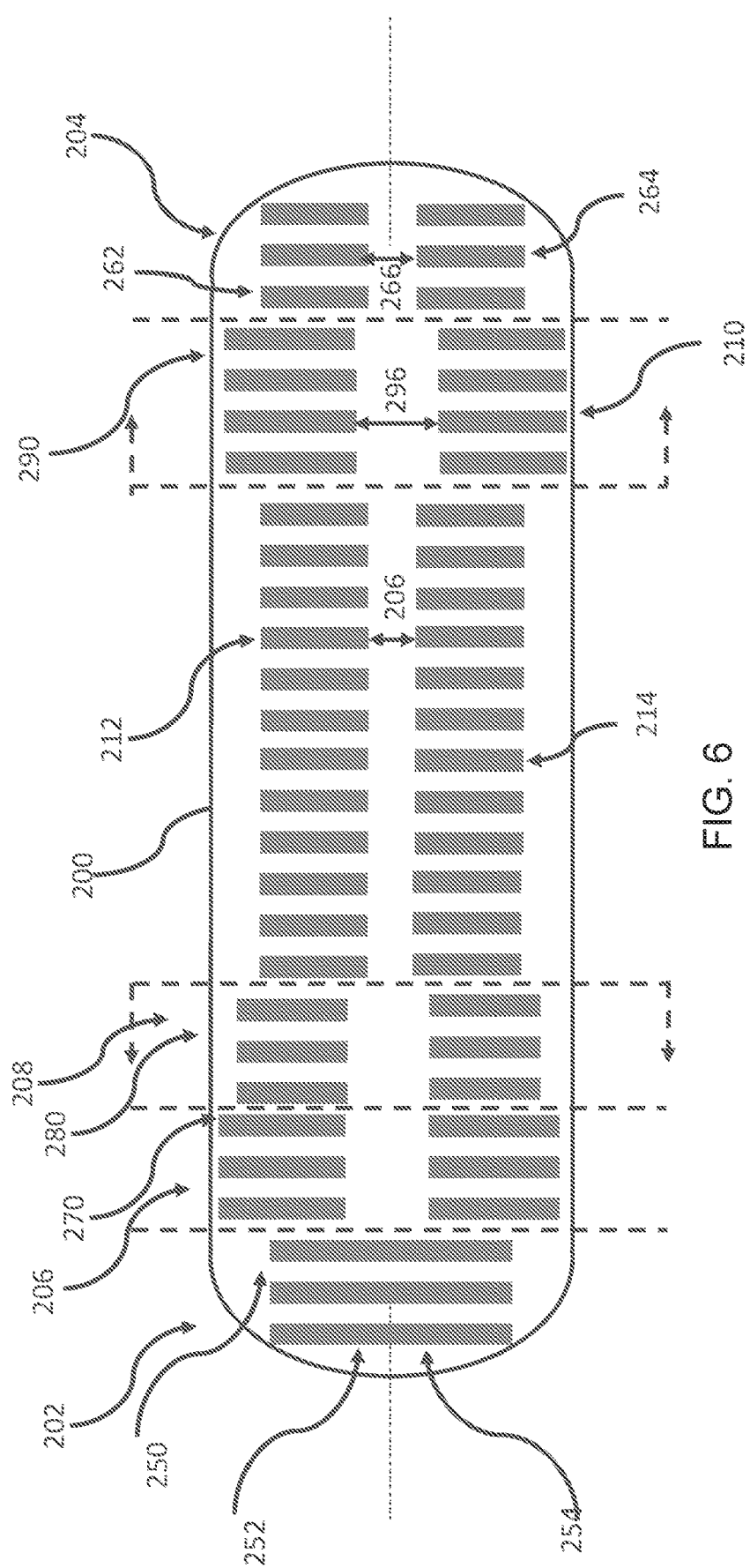
FIG. 6 represents an absorbent article according to the invention featuring an alternative fastening adhesive pattern.

FIG. 6 shows a further embodiment having a central section 200, front section 202, rear section 204 and additional front and rear sections 206, 208, 210. The shape of the general outline of the respective adhesive stripes has a silhouette form that tapers at the front and rear and at a waist section in the middle. The lengths of the respective stripes and distances of the outer edge of the respective stripes to the outer edge of the absorbent article is chosen to optimize the trade off between the need for greater comfort and effective adhesion. As with previous embodiments, the central section is provided with a first pattern of adhesive formed of a first 212 and second 214 plurality of stripes and a first gap extending over the longitudinal axis between the first and second pluralities. The first gap ensures that the absorbent article may bend along the longitudinal axis when in situ, as this is the area that fits most snugly between a user's legs.

A second pattern of adhesive 250 is provided at the front tip of the absorbent article and is formed of a third 252 and fourth 254 plurality of stripes. A second gap may be provided between the third and fourth plurality of stripes, however, in the embodiment shown in FIG. 6, no gap is provided between the third and fourth plurality of stripes. Where the second gap is missing, the absorbent article may allow the absorbent article to remain flat along the abdomen area of a user. A third pattern 260 of adhesive is provided at the rear tip of the absorbent article and is formed of a fifth and sixth plurality of stripes. A third gap 266 is provided between the fifth 262 and sixth 264 plurality of stripes, although it will be appreciated that in some embodiments, no gap may be provided between the fifth and sixth pluralities of stripes.

Fourth 270 and fifth 280 patterns of adhesive are provided between the front tip and the central section of the absorbent article. The fourth pattern of adhesive is positioned adjacent the second pattern of adhesive and the fifth pattern is provided between the fourth pattern and the first pattern. The fourth and fifth patterns are respectively formed of seventh and eighth and ninth and tenth pluralities of stripes, with a fourth gap between the seventh and eight pluralities of stripes and a fifth gap between the ninth and tenth pluralities of stripes. Again, an absorbent article may be envisioned without the fourth and fifth gaps. However, where the fourth and fifth gaps are provided, the absorbent article is more easily able to bend inwards to better conform to the anatomy of the user. Stripes of the fourth and fifth patterns are located nearer the longitudinal edges of the absorbent article than stripes of the first or second patterns. The positioning of at least the fourth pattern often coincides with the area where the absorbent article may be at its widest. Providing stripes adjacent the edges of the absorbent article in the region where it is widest reduces the likelihood of the absorbent article rolling in on itself when in situ.

Stripes of the second pattern are positioned inboard from the longitudinal edge relative to stripes of the fourth pattern. This creates an arcuate profile along the perimeter of the adhesive that roughly corresponds to the outer perimeter of the absorbent article. Stripes of the fifth pattern a positioned slightly inboard from the longitudinal edge of the absorbent article compared with stripes of the fourth pattern and stripes of the first pattern (in the central section) are positioned slightly inboard from the longitudinal edge of the absorbent article compared with stripes of the fifth pattern. Thus the external profile of the adhesive curves towards a waist in the central section of the absorbent article, typically the narrowest part of the absorbent article and the area typically required to be most flexible when in situ.

A sixth pattern 290 of adhesive is provided between the third pattern and the first pattern. The sixth pattern comprises an eleventh and twelfth plurality of stripes with a sixth gap extending over the longitudinal axis provided therebetween. The stripes of the sixth pattern are located proximal to the longitudinal edge of the absorbent article relative to stripes of the first or third patterns. Typically, the stripes of the sixth pattern would coincide with the widest part of the absorbent article. Providing stripes adjacent the longitudinal edge in the widest part of the absorbent article minimizes the chance of the absorbent article rolling in on itself when in use.

The sixth gap 296 is preferably wider than the first gap to allow bending in the gluteal groove are when the absorbent article is in situ. In an embodiment, the width of the first, third, fourth and fifth gaps may be substantially the same. Preferably, the first, third, fourth and fifth gaps have a width of between 10 mm to 30 mm, the second gap has a gap of less than 10 mm, and the sixth gap has a width of between 20 mm to 40 mm.

Preferably, the stripes of the fourth and sixth patterns have a distance from the outer edge of the respective stripes to the longitudinal edge of the absorbent article of between 5 mm to 10 mm. From the embodiment shown in FIG. 6, it can be seen that the additional adhesive patterns provided enable variation of the positioning and sizing of stripes to best fit the needs of an absorbent article.

The basis weight of the adhesive applied may be between 12 gsm to 22 gsm. Preferably, there is a variation of no more than 5 gsm along the length of individual stripes. Maintaining an even application of adhesive along the individual stripes ensures that the force required to peel off the absorbent article from an undergarment, or to peel off a wrapper from the absorbent article prior to use, remains substantially constant. This minimizes the risk of tearing of the backsheet or of adhesive residue being left on the undergarment after use.

In addition to providing greater flexibility, the striped patterns exemplified herein maintain close contact of the absorbent article with a user's undergarments while reducing the amount of adhesive required. The reduced amount of adhesive has cost and environmental benefits and reduces the amount of force required to peel the absorbent article from an undergarment after its use.

Preferably, the force required to bend an absorbent article as described herein towards the longitudinal axis, as described in the bunch compression test method below, is less than 1.75N, preferably less than 1.7N, 1.65N, 1.6N, 1.55N, 1.5N when wet, and less than 2.3N, 2.2N, 2.1N, 1.0N, 1.9N or 1.8N when dry. The reduced force required to bend the absorbent article in this way is an indication of the increased flexibility of the absorbent article and this is consistent when the article is wet or dry. This, in turns, relates to better comfort and fit for the wearer, particularly in the central sections where flexibility is most desirable.

Preferably, the force required to peel the absorbent article from an undergarment to which it is attached, as measured by the Average Peel force method described below, is less than 2.3N, 2.2N, 2.1N, 1.0N, 1.9N or 1.8N. The reduced force required to remove the absorbent article provides for easier use for the wearer when removing the article and reduces the likelihood of the absorbent article tearing during removal. Each of the above advantages does not come with any reduction in adhesive properties, thus the adhesive pattern described herein functions as required to ensure the absorbent article remains in place, while providing these additional benefits.

Test Data

Figure 7C:
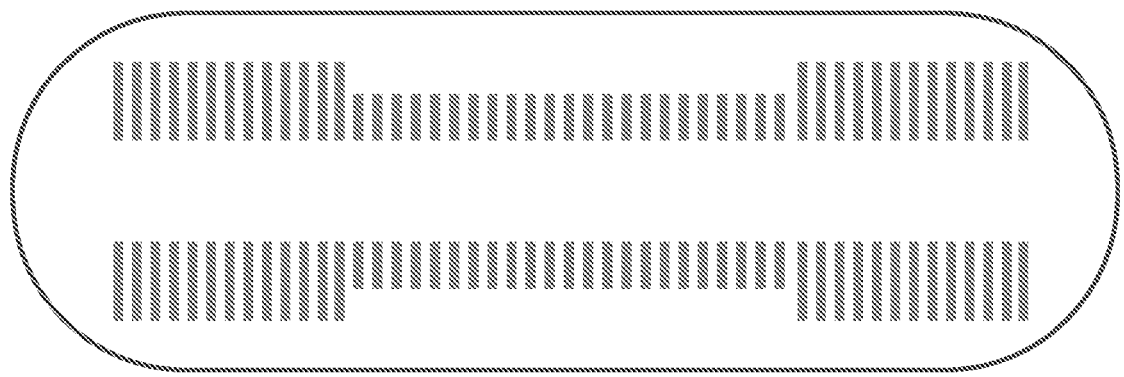
FIGS. 7B and 7C are illustrations showing adhesive patterns of absorbent articles according to the invention.
Figure 7B:
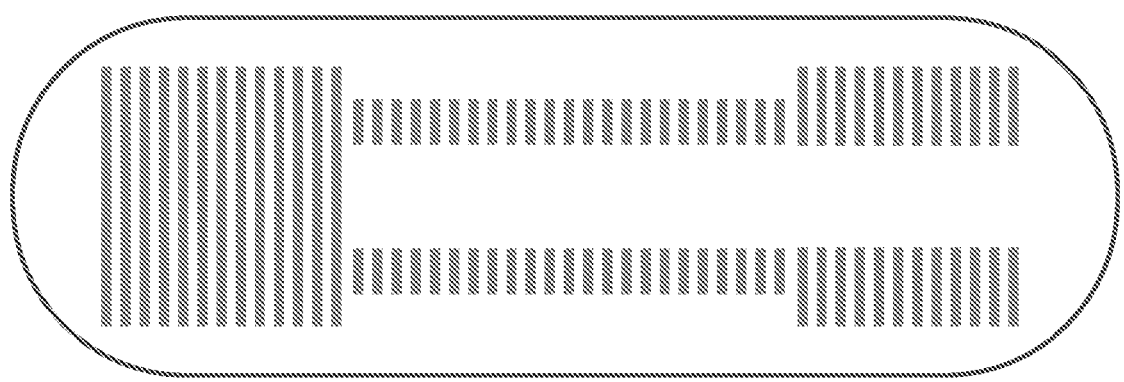

A comparison of the peel-off force and transverse compression stiffness was carried out between an absorbent article of the prior art (shown in FIG. 7A) and an absorbent article of the present invention (shown in FIG. 7B). Additional details pertaining to the two absorbent articles are laid out in Table 1 below.

TABLE 1

Figure 7A:
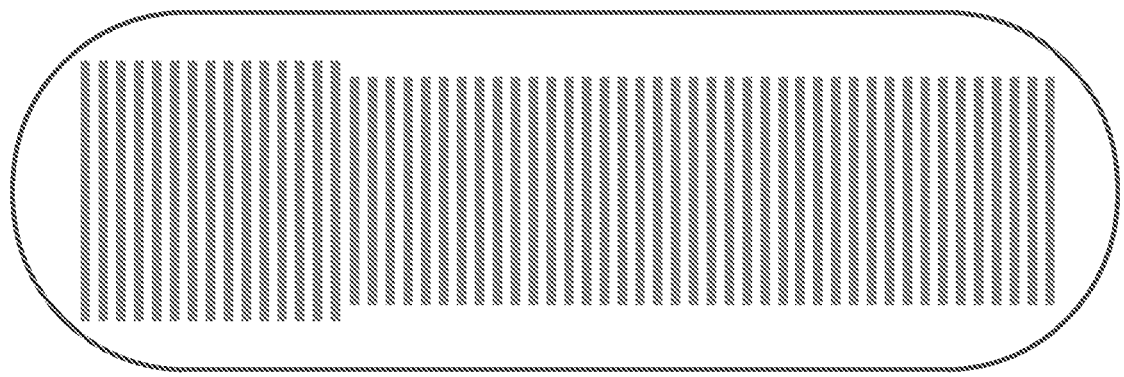
FIG. 7A is an illustration showing the adhesive pattern on a commercially available absorbent article.

|  | Reference (Prior Art) | Inventive Sample 1 | Inventive Sample 2 |
| --- | --- | --- | --- |
| General Structure of Absorbent Article | | | |
| Total length of absorbent article | 284 mm | 284 mm | 284 mm |
| Backsheet | Microporous polyethylene film 12 gsm | Microporous polyethylene film 12 gsm | Microporous polyethylene film 12 gsm |
| Topsheet | Formed film 24.8 gsm | Formed film 24.8 gsm | Formed film 24.8 gsm |
| Absorbent Core | 75% cellulose; 20% AGM 163 gsm | 75% cellulose; 20% AGM 163 gsm | 75% cellulose; 20% AGM 163 gsm |
| Adhesive | | | |
| Adhesive pattern | FIG. 7A | FIG. 7B (schematic illustration: FIG. 4) | FIG. 7C (schematic illustration: FIG. 2) |
| Adhesive Type | Hot-Melt Adhesive* | Hot-Melt Adhesive* | Hot-Melt Adhesive* |
| Adhesive Basis Weight | 12.35 gsm | 15 gsm | 15 gsm |

TABLE 1-continued

|  | Reference (Prior Art) | Inventive Sample 1 | Inventive Sample 2 |
|---|---|---|---|
| Front Section | | | |
| Length of front section | 80 mm | 80 mm | 80 mm |
| Width of front section (measured at widest point) | 90 mm | 90 mm | 90 mm |
| Distance from outer edge of stripe to outer edge of absorbent article | 10 mm | 20 mm | 20 mm |
| Stripe width | 2 mm | 2 mm | 2 mm |
| Stripe length (front section) | 50 mm (combined length of stripes either side of longitudinal axis) | 55 mm (combined length of stripes either side of longitudinal axis) | 18 mm (individual stripes either side of longitudinal axis) |
| Longitudinal gap | 2 mm | 2 mm | 2 mm |
| $2^{nd}$ Gap width | N/A | N/A | 25 mm |
| Central Section | | | |
| Length of central section | 124 mm | 124 mm | 124 mm |
| Width of central section (measured at widest point) | 95 mm | 95 mm | 95 mm |
| Distance from outer edge of stripe to outer edge of absorbent article | 10 mm | 20 mm | 20 mm |
| Stripe width | 2 mm | 2 mm | 2 mm |
| Stripe length | 50 mm (combined length of stripes either side of longitudinal axis) | 10 mm | 10 mm |
| First gap | N/A | 25 mm | 25 mm |
| Longitudinal gap | 2 mm | 2 mm | 2 mm |
| Rear Section | | | |
| Length of rear section | 80 mm | 80 mm | 80 mm |
| Width of rear section (measured at widest point) | 90 mm | 90 mm | 90 mm |
| Distance from outer edge of stripe to outer edge of absorbent article | 10 mm | 20 mm | 20 mm |
| Stripe width | 2 mm | 2 mm | 2 mm |
| Stripe length (rear section) | 58 mm (with no $2^{nd}$ gap) | 18 mm | 18 mm |
| Third gap width | N/A | 25 mm | 25 mm |
| Longitudinal gap | 2 mm | 2 mm | 2 mm |

*Savare SRL Milan, marketed as PL501ZK

TABLE II

|  | Reference | Inventive sample 1 | Inventive sample 2 |
|---|---|---|---|
| Average Peel Force (N) | 2.37 | 1.98 | 1.62 |
| Average Bunch Compression Force (Dry) (N) | 2.43 | 1.73 | 1.69 |
| Average Bunch Compression Force (Wet) (N) | 1.81 | 1.37 | 1.48 |

Figure 8:
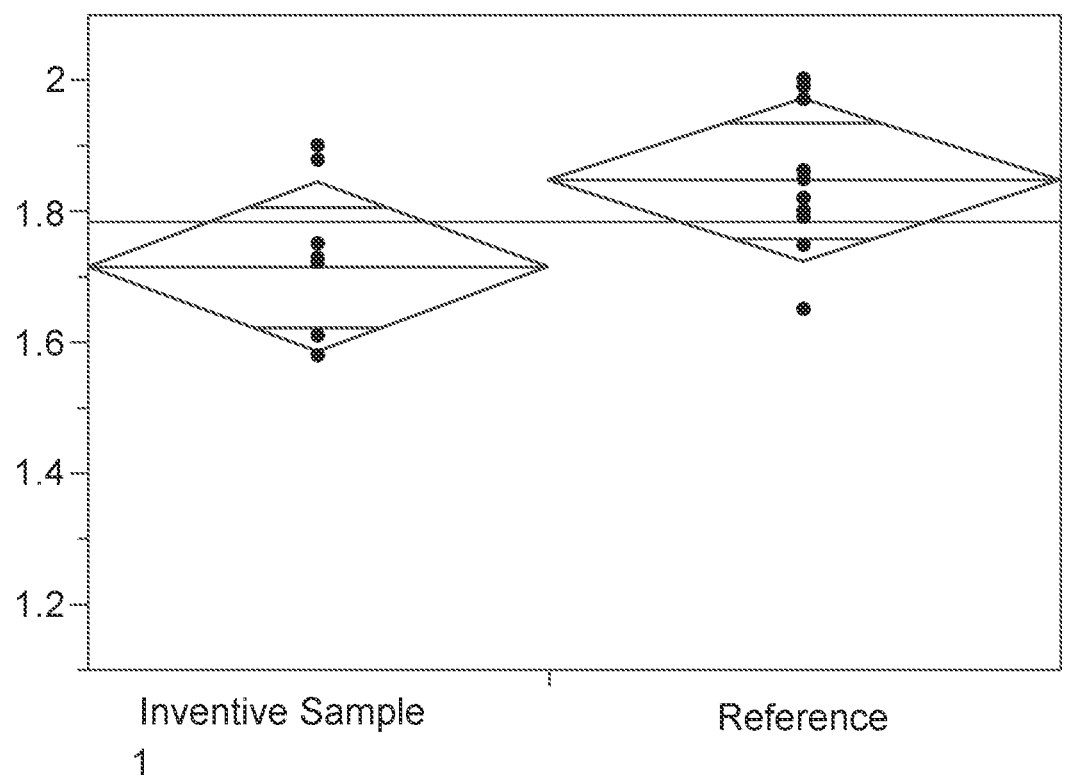
FIG. 8 is a comparison of the peel-off force required in the invention vs the prior art.
Figure 9A:
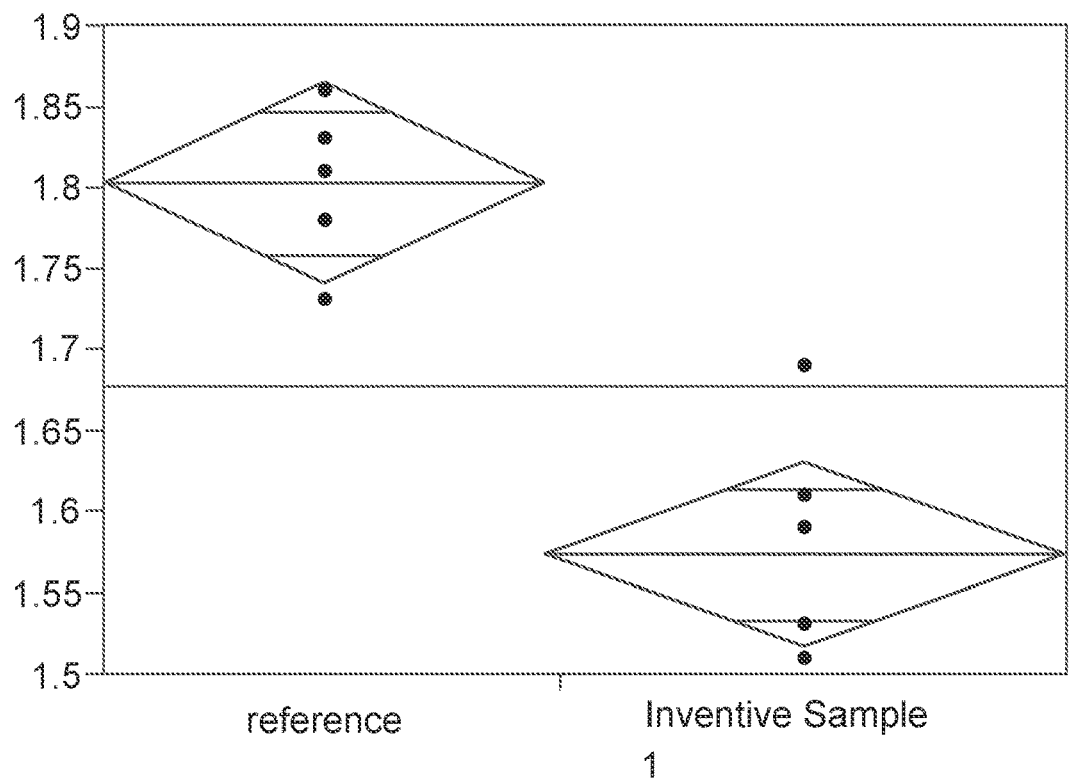
FIGS. 9A and 9B are comparisons of the bunched compression of an absorbent article of the invention vs the prior art.
Figure 9B:
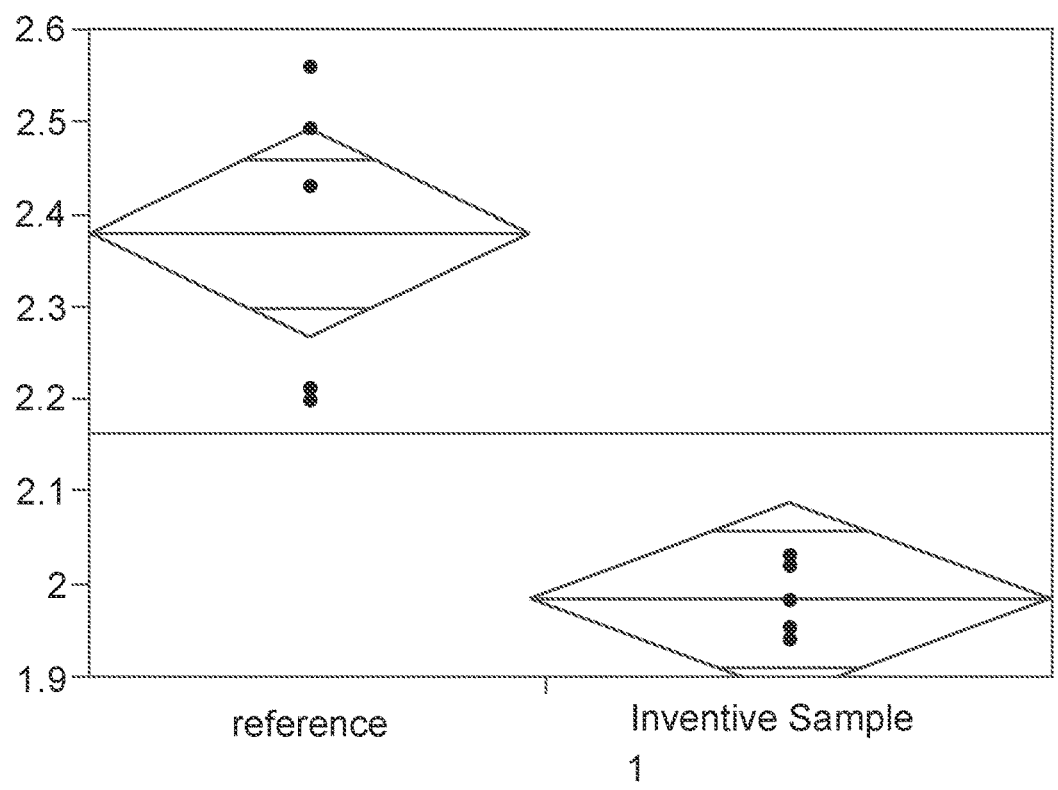

From Table II and the accompany graphs shown in FIGS. 8, 9A and 9B, it can be seen that the Inventive Samples perform better than the reference samples across different parameters. Specifically, the force required to peel the absorbent article from an undergarment is shown to be less for both inventive samples (Average Peel Force). Without being bound by theory, it is thought that this is caused at least in part by the reduction in amount of adhesive, while the inventive distribution ensures that the absorbent article remains in place. Furthermore, the force required to bend the absorbent articles, as measured by the Bunch Compression Force test that measures the force required to compress an absorbent article in the transverse direction, is less for the inventive samples. This provides an indication that the patterns of adhesive applied to the inventive samples reduces the overall stiffness of the absorbent articles, while again, still maintaining a good level of adhesion. The reduced stiffness in turn means that the absorbent articles better move together with the undergarments, that are usually not stiff, and better conform to the body of the wearer.

Optional wings (also called "side panels") are common elements in absorbent articles according to the present invention as known to the persons skilled in the art. The intent of the wings is to protect the sides of the undergarments and typically wings fold along the crotch area of the underwear and are attached below it.

Wings can be provided as separate pieces and be attached to the article, typically a pantyliner or a sanitary napkin, or they can be integral with the materials of the absorbent articles, e.g., by being an integral extension of the topsheet, the backsheet, or of both.

As mentioned above, for the purpose of the present invention, wings are not considered part of the backsheet (even when they are formed by an integral extension of it). Wings typically include PFA on the backsheet side in order to affix them below the crotch of the underwear, and any typical PFA distribution can be used in the present invention, such as a continuous application or a patterned application, for example a patterned application of PFA on the wings may provide the same benefits as the patterned PFA application on the backsheet of the article when the article is removed thus reducing the risk of tearing the wing material. For example at least a portion of the wing back surface can comprise a patterned application of PFA in the same forms described above for the patterned PFA application on the backsheet e.g. a discontinuous application of the PFA such that any point of said application is never more than 10 mm distant from another portion where PFA is not applied. The PFA pattern can be formed by a plurality of separate or only partially connected elements which can be selected from any possible application pattern such as for example stripes, circles, dots, geometric figures, stars, decorative figures, irregular shapes, and the like. For example stripes or squares of PFA are particularly suitable patterns.

Test Methods.

Pad and PFA Dimension Measurements

Analysis of a photographic image obtained for an absorbent article is used to determine the dimensions (e.g. length, width, area) of the article and the dimensions (e.g. length, width, area and spacing) of the individual elements that make up the Panty Fastening Adhesive (PFA) pattern that is applied to the garment-facing side of the article. All testing is performed in a room maintained at a temperature of 23° C.±2.0° C. and a relative humidity of 50%±2% and samples are conditioned under the same environmental conditions for at least 2 hours prior to testing.

To prepare the test sample, first remove it from any wrapper present, but leave the PFA protective cover (e.g. release paper wrapper) in place. If the wrapper is the protective cover (e.g. PFA is attached directly to the wrapper), then leave the wrapper in place. If the sample is folded, gently unfold it and smooth out any wrinkles. If wings are present, leave them folded against the wearer-facing side of the sample. Apply a strip of double-sided tape to the wearer-facing side of the sample about 1 cm from each longitudinal edge, then secure it to a horizontally flat surface (wearer-side facing down). Now remove the PFA protective cover (e.g. release paper or wrapper) from the garment-facing side of the sample to expose the PFA pattern. To make the PFA pattern easily visible, lightly dust the PFA with marking chalk (such as Keson ProChalk in blue, available from Keson Industries, Aurora, IL, or equivalent). Dust off any excess to ensure that areas that do not contain adhesive are free of the colored chalk.

Obtain a photographic image of the sample as follows. Transfer the sample to a horizontally flat surface that provides adequate contrast with the garment-facing side of the sample. Then secure the wearer-facing side to the surface (using the previously applied double sided tape strips) in a taut but unstretched manner with the garment-facing side up. A distance scale (NIST certified steel ruler) is placed horizontally flat next to the sample. Collect an 8 bit grayscale image with either a digital camera or flat bed scanner, with a minimum image resolution of 15 pixels per millimeter. The entire sample and ruler must be visible and focused within the field of view.

The sample image is spatially calibrated and analyzed using image analysis software. A suitable software is ImageJ, distributed by the National Institute of Health, or equivalent. The image is opened in the image analysis program and a linear distance calibration is performed using the ruler within the image to determine the number of pixels per millimeter. From the spatially calibrated image, one can now determine the overall sample dimensions (e.g. length, width, area), dimensions of the overall PFA pattern (e.g. length, width, overall area), as well as dimensions of individual elements within the PFA pattern (e.g. length, width and area of stripes and spaces or gaps between). One suitable way to determine the area of an individual element is to trace around the element and measure the area of the trace. All linear measurements are recorded to the nearest 0.1 mm and all area measurements are recorded to the nearest 0.1 mm$^2$. Of specific importance in this execution is the determination of the total surface area covered by all of the combined individual elements that make up the PFA pattern on the sample. To obtain the Total PFA Surface Area, the areas of each individual element (e.g. each stripe, or other shape) are determined, summed and reported to the nearest 0.1 mm$^2$.

In like fashion, a total of three replicate samples are prepared and analyzed. The arithmetic mean for each measured parameter is calculated and reported.

PFA Add-On Measurement

The quantity (basis weight) of Panty Fastening Adhesive (PFA) applied to the garment-facing side (e.g. backsheet) of an absorbent article is determined gravimetrically by comparing the mass of the backsheet that has PFA applied to the mass of the same backsheet after the PFA has been removed. All testing is performed in a room maintained at a temperature of 23° C.±2.0° C. and a relative humidity of 50%±2% and samples are conditioned under the same environmental conditions for at least 2 hours prior to testing.

Prepare the test sample as follows. If the sample is folded, gently unfold it but leave the PFA protective cover (e.g. release paper and/or wrapper) in place. If wings are present, remove them and discard. Now remove and discard all components present in the sample on the wearer-facing side of the backsheet, in a manner that does not damage the backsheet. This includes the topsheet and all core materials so that once removed and discarded, all that is left of the sample is the backsheet and the PFA protective cover. Transfer the sample to a sufficiently ventilated fume hood and don the appropriate personal protective equipment (PPE) required for handling THF (tetrahydrofuran, CAS 109-99-9, for general use, available from any convenient source). Position the sample horizontally flat with the garment-facing side of the sample facing down. Apply a sufficient amount of THF to a paper towel and wipe the wearer-facing side of the backsheet to remove all remnants of the core and core adhesive. Several passes using fresh paper towels and THF will likely be required to remove all of the core adhesive. Allow the sample to thoroughly dry in the fume hood.

Obtain the mass of the dried sample (e.g. backsheet, PFA, and PFA protective cover) and record as Initial Mass to the nearest 0.01 mg. Transfer the sample back to the fume hood and once again don the appropriate PPE required for handling THF. Position the sample horizontally flat with the garment-facing side of the sample facing up. Remove the PFA protective cover (e.g. release paper and/or wrapper) and set aside for later use. Apply a sufficient amount of THF to a paper towel and wipe the garment-facing side of the backsheet to remove all of the PFA. Several passes using fresh paper towels and THF will likely be required to remove all of the PFA. Allow the sample to thoroughly dry in the fume hood. Obtain the mass of the dried sample (e.g. backsheet and previously removed PFA protective cover) and record as Final Mass to the nearest 0.01 mg. Calculate the PFA Add-On by subtracting the Final Mass from the Initial Mass and record to the nearest 0.01 mg.

In like fashion, a total of three replicate samples are prepared and analyzed. The arithmetic mean for PFA Add-On is calculated and reported to the nearest 0.01 mg.

The PFA Basis Weight can be determined using the mean PFA Add-On value obtained from this method and the Total Adhesive Surface Area value obtained from the mean PFA Dimension method. Calculate and report the PFA Basis Weight to the nearest 0.01 g/m² using the following equation.

PFA Basis Weight (g/m²)=[PFA Add-On (mg)/Total PFA Surface Area (mm²)]*1000

Bunch Compression Test

Bunched Compression of a sample is measured on a constant rate of extension tensile tester (a suitable instrument is the MTS Alliance using Testworks 4.0 software, as available from MTS Systems Corp., Eden Prairie, Minn., or equivalent) using a load cell for which the forces measured are within 10% to 90% of the limit of the cell. All testing is performed in a room controlled at 23° C.±3° C. and 50%±2% relative humidity. The test can be performed wet or dry.

Figure 10:
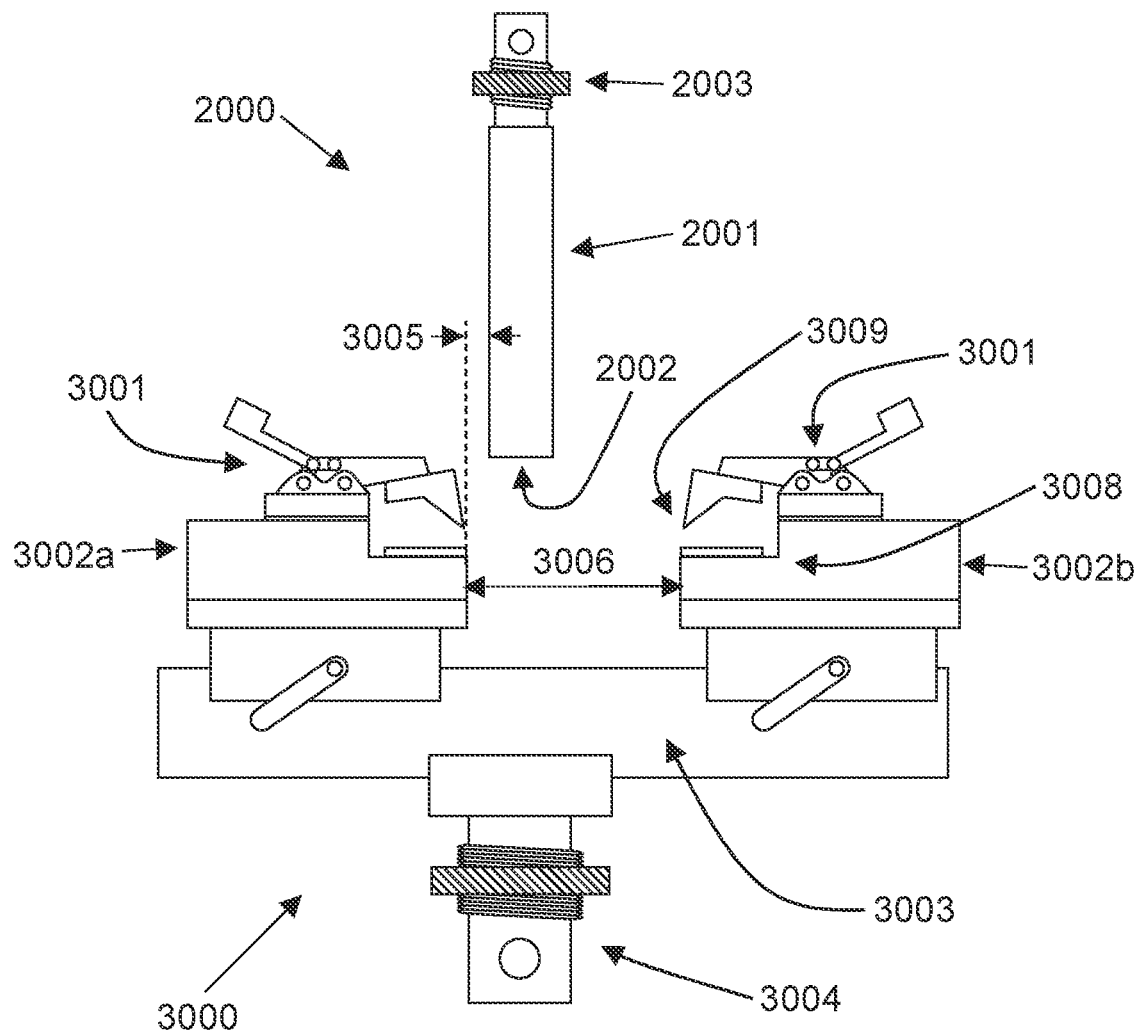
FIGS. 10, 11A, 11B, 12A & 12B illustrate schematically test apparatus used in the present invention.

The test apparatus is depicted in FIGS. 10 to 12. The bottom stationary fixture 3000 consists of two matching sample clamps 3001 each 100 mm wide, each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3° C. and 50%±2% relative humidity for at least 2 hours before testing. When testing a whole article, remove the release paper from any panty fastening adhesive on the garment facing side of the article if present. Lightly apply talc powder to the adhesive to mitigate any tackiness. If there are cuffs, excise them with scissors, taking care not to disturb the top sheet of the product. Place the article, body facing surface up, on a bench. On the article, identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines.

The specimen can be analyzed both wet and dry. The dry specimen requires no further preparation. The wet specimens are dosed with 0.9% w/v saline solution (i.e., 9.0 g of reagent grade NaCl diluted to 1 L deionized water). The volume of liquid added to the specimen is determined by the overall length of the pad being tested, according to the table below.

| Pad Length (mm) | Volume (mL) |
|---|---|
| <225 | 4.5 |
| 226-250 | 6 |
| 251-275 | 10 |
| 276-320 | 15 |
| 321-350 | 20 |
| 351-375 | 25 |
| >375 | 30 |

The dose is added using a calibrated Eppendorf-type pipettor, spreading the fluid over the complete body facing surface of the specimen within a period of approximately 3 sec. The wet specimen is tested 10.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 11A:
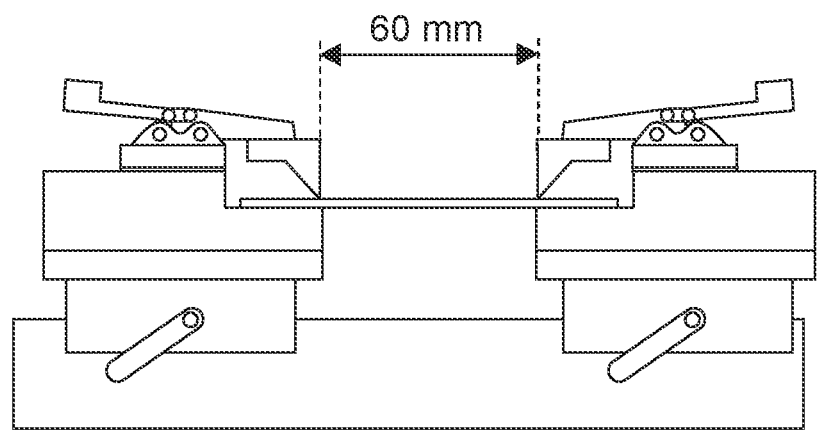
Figure 11B:
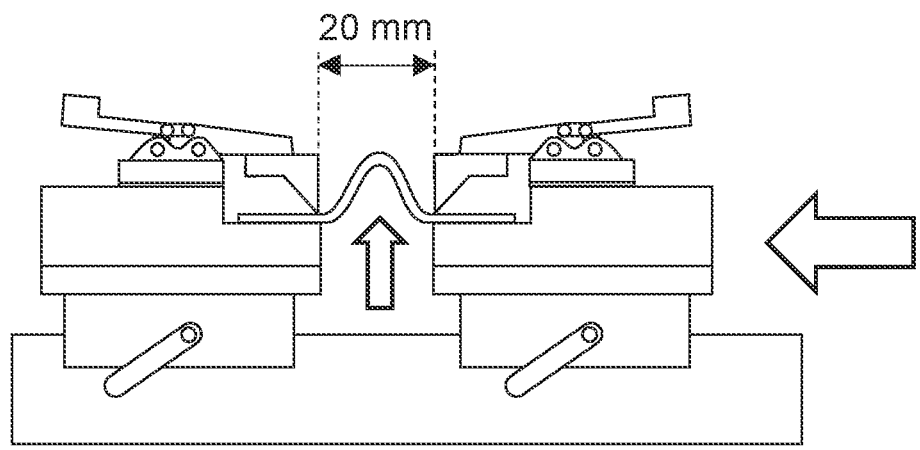

Position the left platform 3002a 2.5 mm from the side of the upper plunger (distance 3005). Lock the left platform into place. This platform 3002a will remain stationary throughout the experiment. Align the right platform 3002b 60.0 mm from the stationary clamp (distance 3006). Raise the upper probe 2001 such that it will not interfere with loading the specimen. Open both clamps 3001. Referring to FIG. 11A, place the specimen with its longitudinal edges (i.e., the 100 mm long edges) within the clamps. With the specimen laterally centered, securely fasten both edges. Referring to FIG. 11B, move the right platform 3002b toward the stationary platform 3002a a distance 20.0 mm. Allow the specimen to bow upward as the movable platform is positioned. Manually lower the probe 2001 until the bottom surface is approximately 1 cm above the top of the bowed specimen.

Figure 12A:
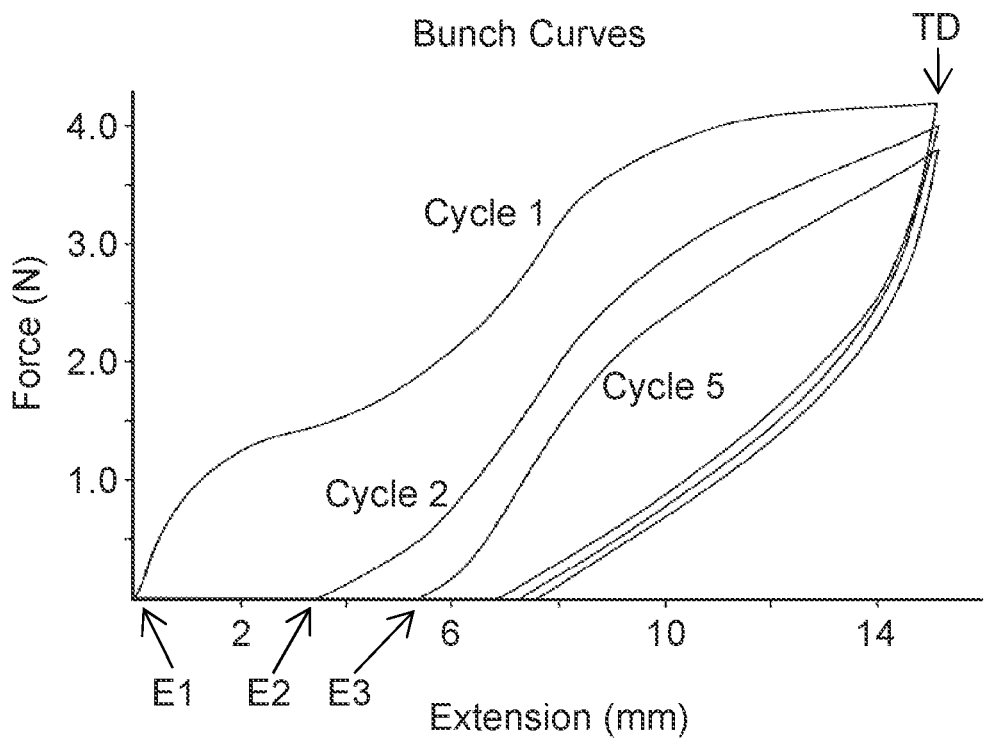
Figure 12B:
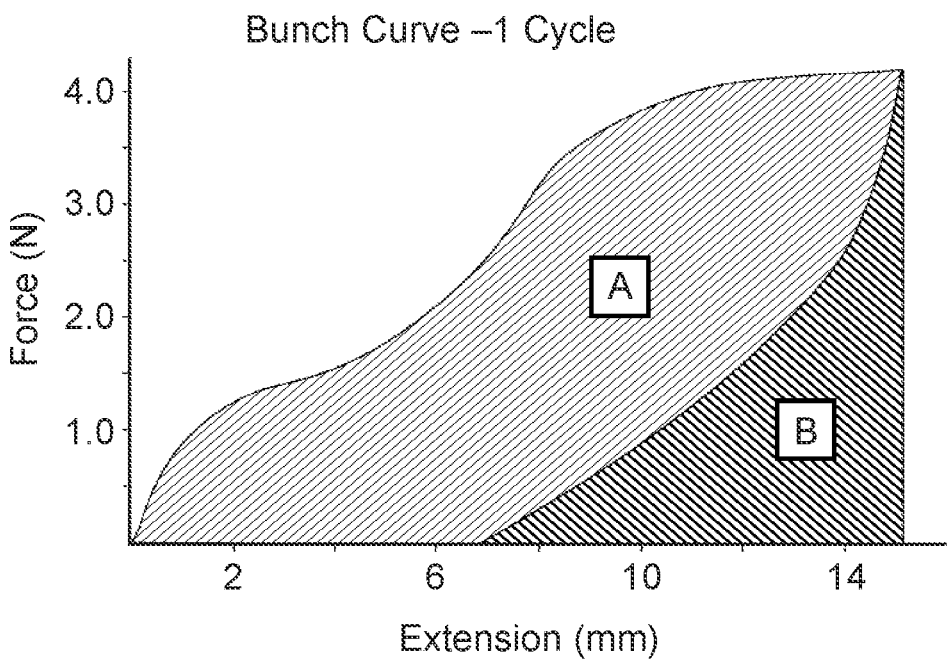

Start the test and collect displacement (mm) verses force (N) data for all five cycles. Construct a graph of Force (N) versus displacement (mm) separately for all cycles. A representative curve is shown in FIG. 12A. From the curve record the Maximum Compression Force for each Cycle to the nearest 0.01N. Calculate the % Recovery between the First and Second cycle as (TD-E2)/(TD-E1)*100 where TD is the total displacement and E2 is the extension on the second compression curve that exceeds 0.02 N. Record to the nearest 0.01%. In like fashion calculate the % Recovery between the First Cycle and other cycles as (TD-Ei)/(TD-E1)*100 and report to the nearest 0.01%. Referring to FIG. 12B, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion calculate the Energy of Compression (mJ), Energy Loss (mJ) and Energy of Recovery (mJ) for each of the other cycles and record to the nearest 0.1 mJ. For each sample, analyze a total of five (5) replicates and report the arithmetic mean for each parameter. All results are reported specifically as dry or wet including the volume of the dose.

Peel Force Test Method (PFA to Undergarment)

This peel force test method is used to determine the force required to peel a strip of standard cotton from the panty fastening adhesive (PFA) on the garment-facing side of an absorbent article. This method is intended to simulate the removal of an absorbent article adhered to a user's undergarment during use. Peel force is measured on a constant rate of extension tensile tester interfaced to a computer (a suitable instrument is the MTS Alliance using Testworks 4.0 software, as available from MTS Systems Corp., Eden Prairie, MN, or equivalent) using a load cell for which the forces measured are within 1%-99% of the limit of the cell. All testing is performed in a room controlled at 23° C.±3° C. and 50%±2% relative humidity and test samples are conditioned in this environment for at least 2 hours prior to testing.

To support the test sample during the peel test, a rigid backing plate (stainless steel with a thickness of about 1.5 mm) is used. The dimensions of the backing plate are governed by the size of the sample being tested as follows. The length of the plate is about 25 mm longer than the overall longitudinal length of the test sample, and the width of the plate is about 10 mm wider than the lateral width of the test sample measured at its widest location (excluding wings).

A strip of cotton is used to simulate the wearer's undergarment. The standard cotton used for this peel test is 100% bleached cotton weave, about 100 g/m² (Style #429W) available from Testfabrics, Inc., West Pittston, PA. Additional distributors of this fabric can be found on the Testfabrics website, www.testfabrics.com. To note, this fabric is sided and the "test side" must be labeled by the supplier. Prepare a strip of the standard cotton that has a width equal to the widest portion of the PFA pattern with a length that is about 30 mm longer than twice the longitudinal length of the PFA pattern on the sample. The cotton strip must be sufficiently wide enough to cover the entire width of the PFA pattern and long enough to cover the entire length of the PFA pattern, overlap itself entirely and still have enough excess leftover to insert into the upper grip of the tensile tester. A fresh cotton strip is used for each sample.

A padded weight assembly is used to ensure adequate and even attachment of the standard cotton strip to the PFA. The weight assembly must impart a pressure of 26-27 g/cm² with a base that has about the same length and width as that of the test sample (width determined at widest location on test sample excluding wings). The weight assembly is constructed as follows. Lay a single layer of polyethylene film (0.02-0.04 mm thick; any convenient source) flat on a bench surface. A piece of flexible insulation foam (Buna-N/PVC, 1 inch thick, density of 4.5 pounds/cubic foot; available from McMaster-Carr, Princeton, NJ, or equivalent) that is cut to the predetermined base size is laid centered on top of the film. A metal weight (same length and width as the predetermined base size) with a handle is then attached to the insulation foam using double sided tape. Next the polyethylene film is wrapped around the insulation foam and secured to the sides of the metal weight using transparent tape.

To prepare the test sample, first remove it from any wrapper present, but leave the PFA protective cover (e.g. release paper) intact. If the wrapper is the protective cover (e.g. PFA is attached directly to the wrapper), then leave the wrapper intact. If the sample is folded, gently unfold it, smooth out any wrinkles and determine which end of the sample is intended to be the front end. If wings are present, unfold the wings. Without disturbing the PFA protective cover, determine the overall length of the PFA pattern using a steel ruler (NIST certified), and record as $PFA_L$ to the nearest mm.

Attach the sample to the backing plate as follows. Lay the backing plate on a horizontally flat rigid surface. With the body facing side of the sample facing down, laterally center the sample over the backing plate and align the front longitudinal edge of the sample within 1 cm from the upper longitudinal edge of the backing plate. The sample is secured to the backing plate using one-sided tape (about 1 inch wide) as follows. The tape is placed no closer than about 1 cm from any portion of the PFA pattern, and no tape is attached to any portion of the PFA protective cover (e.g. release paper, wrapper). Secure the front end of the sample to the backing plate by overlapping the end of the sample with a strip of tape positioned approximately parallel to the lateral axis of the sample. Now pull the sample taut to remove any wrinkles and secure the back end of the sample to the backing plate by overlapping the end of the sample with a strip of tape positioned approximately parallel to the lateral axis of the sample. If the sample does not contain wings, secure the entire length of the lateral edge on both sides of the sample to the backing plate using strips of tape. If the sample contains wings, fold each wing around the lateral edges of the backing plate and secure to the backside of the plate with tape. Then in like fashion, secure the remaining length of the lateral edge on both sides of the sample to the top side of the backing plate. The sample is secured in such a way that it is held taut without stretching to keep it flat against the backing plate during the peeling process. In instances where the PFA covers the entire backsheet, tape is used only at the front and back edges of the sample such that the tape overlaps each end by no more than about 1 cm.

After the sample has been secured to the backing plate and still lying on a flat rigid surface with the PFA side of the sample facing up, attach the prepared strip of standard cotton as follows. Remove the PFA protective cover from the sample and determine whether the PFA pattern is continuous in the longitudinal direction (e.g. one or more stripes with no lateral spaces along its longitudinal length). Measure the overall longitudinal length of the PFA pattern and record as $PFA_L$ to the nearest 0.1 mm. Now laterally center the cotton strip over the sample ("test side" facing the sample). Position the leading edge of the cotton strip at a distance no more than 1 cm above the front edge of the PFA pattern. Ensure the longitudinal axis of the cotton strip is aligned with the longitudinal axis of the sample and secure it to the front edge of the PFA pattern. Continue to apply the cotton strip over the remaining portion of the PFA pattern without creating any wrinkles in the cotton or sample. By design, there will be an excess length of cotton trailing off the back longitudinal end of the sample, referred to as the trailing end of the cotton strip. Center and then place the prepared weight assembly over the sample on top of the attached cotton strip. After 30±2 seconds have elapsed, remove the weight assembly and set it aside. The sample is now prepped for testing and must be analyzed within 1 minute after the weight assembly has been removed.

Program the tensile tester for a constant rate of extension uniaxial elongation with a set path length as follows. The gauge length is governed by the length of the backing plate, and is set to a distance that is about 10 mm greater than the length of the backing plate that will not be within the lower grip. The gauge length is set using a calibrated ruler traceable to NIST, or equivalent. Zero the crosshead and load cell. The path length is governed by the length of the PFA pattern, PFA$_L$, and is set to a distance that is about 5 mm greater than PFA$_L$. Without disturbing the attached strip of cotton, insert about 10 mm of the bottom longitudinal edge of the backing plate (where the back end of the test sample is secured) into the grip of the bottom fixture of the tensile tester ensuring that no part of the sample is within the grip. The backing plate must be centered and parallel to the central pull axis of the tensile tester. Now insert the trailing end of the cotton strip into the grip of the upper fixture of the tensile tester. Ensure the cotton strip is centered and parallel to the central pull axis of the tensile tester. Adjust the amount of the cotton strip in the upper grip in order to minimize the slack of cotton at the back end of the PFA pattern, and ensure there is ≤0.1 N of tension to prevent pre-mature peeling. Raise the crosshead at a rate of 1016 mm/min for the entire path length, collecting force (N) and extension (mm) data at 50 Hz throughout the test. Return the crosshead to its original location. Construct a graph of force (N) versus extension (mm).

For test samples that have a PFA pattern that is continuous in the longitudinal direction, calculate the Average Peel Force ($F_a$) along the path length, excluding all datapoints within the initial and final 1 cm of path length, and record to the nearest 0.01 N. In like fashion, repeat the test for a total of five replicate test samples. Calculate the arithmetic mean for Average Force ($F_a$) and report as Average Peel Force to the nearest 0.01 N.

For test samples that have a PFA pattern that is not continuous in the longitudinal direction (e.g. one or more spaces present along its longitudinal length), the resultant graph will consist of a series of peaks (adhesive region) and valleys (non-adhesive region). For this type of sample, the maximum force at each peak along the path length, excluding all datapoints within the initial and final 1 cm of path length, is recorded to the nearest 0.01 N. Now calculate the Average of Peak Peel Forces ($F_p$) for all of the peaks and record to the nearest 0.01 N. In like fashion, repeat the test for a total of five replicate test samples. Calculate the arithmetic mean for Average of Peak Forces ($F_p$) and report as Average of Peak Peel Forces to the nearest 0.01 N.

In all cases where a percentage is mentioned within the present application it is intended to be a percentage by weight, unless specified otherwise.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. An absorbent article having a central longitudinal axis and a transverse axis perpendicular to the longitudinal axis, the absorbent article comprising:
    a) a front section, a central section and a rear section located along the longitudinal axis;
    b) a backsheet having a garment facing surface;
    c) a first pattern of fastening adhesive applied to the central section of the garment facing surface of the backsheet, the first pattern of adhesive comprising:
        i) a first plurality of stripes extending substantially parallel to the transverse axis on a first side of the central longitudinal axis;
        ii) a second plurality of stripes extending substantially parallel to the transverse axis on a second side of the central longitudinal axis; and
        iii) a first gap between the first plurality of stripes and the second plurality of stripes, wherein the first gap extends over the central longitudinal axis; and
    d) a second pattern of fastening adhesive applied to the front section of the garment facing surface of the backsheet, the second pattern of adhesive comprising:
        i) a third plurality of stripes extending substantially parallel to the transverse axis on said first side of the longitudinal axis; and
        ii) a fourth plurality of stripes extending substantially parallel to the transverse axis on said second side of the longitudinal axis, wherein no gap is provided across the longitudinal axis between the third plurality of stripes and the fourth plurality of stripes.

2. An absorbent article as claimed in claim 1, wherein the first gap has a width substantially parallel to the transverse axis, wherein the width is between about 15 mm and 35 mm.

3. An absorbent article as claimed in claim 1, wherein said stripes of said first plurality and said second plurality have a length substantially parallel to the transverse axis, and a width substantially parallel to the longitudinal axis, wherein the length of each stripe is between 5 mm to about 30 mm and the width is between 1 mm and 5 mm.

4. An absorbent article as claimed in claim 1, wherein said first plurality of stripes further comprises longitudinal gaps between adjacent stripes, wherein the longitudinal gaps are between about 1 mm and 10 mm.

5. An absorbent article as claimed in claim 1, wherein each stripe has an outer edge, wherein the distance between the outer edge of stripes in the first pattern and a corresponding outer edge of the absorbent article is between 10 mm and 30 mm.

6. An absorbent article as claimed in claim 1, wherein the stripes of the first and second plurality combined extend across between 10% and 85% of the width of the absorbent article.

7. An absorbent article as claimed in claim 1, wherein the central section has a total area, wherein an area of the central section covered by adhesive is between 10% and 85% of the total area of the central section.

8. An absorbent article as claimed in claim 1, wherein a bunch compression force for said absorbent article measured when wet is less than 1.75N.

9. An absorbent article as claimed in claim 1, wherein a bunch compression force for said absorbent article measured when dry is less than 2.30N.

10. An absorbent article as claimed claim 1, wherein the average peel force is less than 2.30N.

* * * * *